(12) United States Patent
Reb et al.

(10) Patent No.: US 9,744,303 B2
(45) Date of Patent: Aug. 29, 2017

(54) PRE-LOADED SYRINGES AND METHODS RELATED THERETO

(71) Applicant: Merit Medical Systems, Inc., South Jordan, UT (US)

(72) Inventors: Philippe Reb, Themericourt (FR); Peter C. Sutcliffe, Palm Coast, FL (US)

(73) Assignee: Merit Medical Systems, Inc., South Jordan, UT (US)

( * ) Notice: Subject to any disclaimer, the term of this patent is extended or adjusted under 35 U.S.C. 154(b) by 13 days.

(21) Appl. No.: 14/327,007

(22) Filed: Jul. 9, 2014

(65) Prior Publication Data

US 2015/0018800 A1   Jan. 15, 2015

Related U.S. Application Data

(60) Provisional application No. 61/844,659, filed on Jul. 10, 2013.

(51) Int. Cl.
| | |
|---|---|
| *A61M 31/00* | (2006.01) |
| *A61M 5/31* | (2006.01) |
| *A61B 17/12* | (2006.01) |
| *A61M 5/00* | (2006.01) |

(52) U.S. Cl.
CPC ..... *A61M 5/3129* (2013.01); *A61B 17/12186* (2013.01); *A61B 2017/1205* (2013.01); *A61M 5/001* (2013.01); *A61M 2005/3131* (2013.01)

(58) Field of Classification Search
CPC ... A61M 31/007; A61M 5/3129; A61M 5/001
USPC ........................................................ 604/507
See application file for complete search history.

(56) References Cited

U.S. PATENT DOCUMENTS

| | | | |
|---|---|---|---|
| 5,338,312 A * | 8/1994 | Montgomery | A61M 5/3129 427/2.3 |
| 7,264,669 B1 | 9/2007 | Tomasino et al. | |
| 7,431,989 B2 * | 10/2008 | Sakhrani | B05D 3/145 428/411.1 |
| 7,553,529 B2 | 6/2009 | Sakhrani et al. | |
| 7,674,504 B2 * | 3/2010 | Sakhrani | B05D 3/145 427/457 |
| 2003/0055386 A1 | 3/2003 | Strauss et al. | |
| 2003/0225391 A1 | 12/2003 | Cragg et al. | |
| 2004/0092883 A1 | 5/2004 | Casey, II et al. | |
| 2008/0145565 A1 * | 6/2008 | Sakhrani | B05D 3/145 427/536 |
| 2008/0254304 A1 | 10/2008 | Sakhrani et al. | |
| 2009/0010985 A1 | 1/2009 | Sakhrani et al. | |
| 2009/0053276 A1 * | 2/2009 | Richard | A61K 9/0019 424/422 |
| 2009/0103074 A1 | 4/2009 | Cuomo et al. | |
| 2009/0126404 A1 * | 5/2009 | Sakhrani | C03C 17/3405 65/30.1 |
| 2010/0298779 A1 | 11/2010 | Hetzler et al. | |
| 2011/0060290 A1 | 3/2011 | Bonk et al. | |
| 2011/0082430 A1 * | 4/2011 | Conzone | A61M 5/31513 604/230 |
| 2012/0171386 A1 | 7/2012 | Bicker et al. | |

FOREIGN PATENT DOCUMENTS

WO      WO 9413345 A1 *  6/1994   ........ A61M 5/31513

OTHER PUBLICATIONS

International Search Report and Written Opinion dated Oct. 30, 2014 for PCT/US2014/045946.

\* cited by examiner

*Primary Examiner* — Edelmira Bosques
(74) *Attorney, Agent, or Firm* — Stoel Rives LLP

(57) ABSTRACT

Pre-loaded syringes for delivering an embolic agent are disclosed herein. Methods related to syringes pre-loaded with an embolic agent are also disclosed.

12 Claims, 4 Drawing Sheets

PRE-LOADED SYRINGES AND METHODS RELATED THERETO

CROSS-REFERENCE TO RELATED APPLICATIONS

Under 35 U.S.C. §119(e), this application claims the benefit of U.S. Provisional Patent Application No. 61/844,659, entitled "PRE-LOADED SYRINGES AND METHODS RELATED THERETO," filed Jul. 10, 2013, the contents of which are hereby incorporated herein by reference in their entirety.

TECHNICAL FIELD

The present disclosure relates generally to medical devices. More specifically, the present disclosure relates to syringes. Even more specifically, the present disclosure relates to pre-loaded syringes for delivery of an embolic agent and methods related thereto.

DETAILED DESCRIPTION

Figure 1:
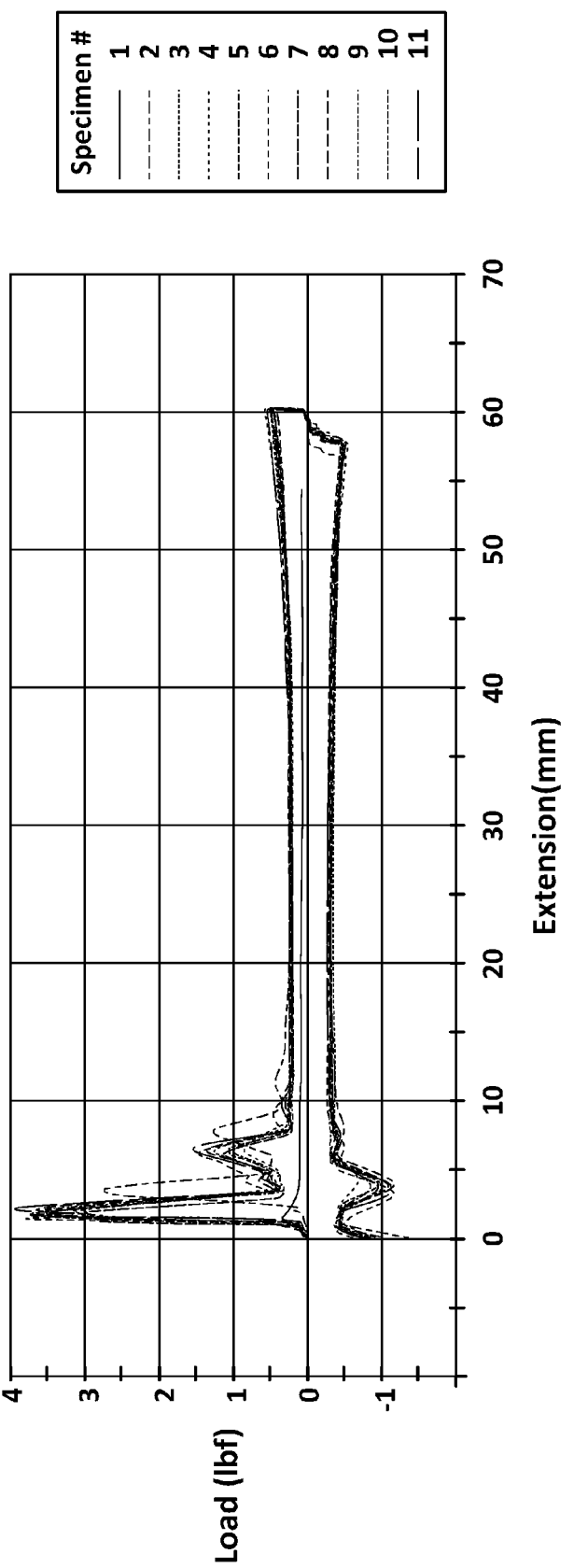
FIG. 1 illustrates the results of force testing (load in pounds-force versus plunger extension) with eleven syringes that were not aged, where the syringes may be used with embodiments of pre-loaded syringes disclosed herein.

It will be readily understood that the components of the embodiments as generally described herein could be arranged and designed in a wide variety of different configurations. Thus, the following more detailed description of various embodiments, as exemplified in the examples, is not intended to limit the scope of the disclosure, but is merely representative of various embodiments.

The phrase "in communication with" refers to any form of interaction between two or more entities, including mechanical, electrical, magnetic, electromagnetic, fluid, and thermal interaction. Two components may be in communication with each other even though they are not in direct contact with each other. For example, two components may be in communication with each other through an intermediate component.

The directional terms "proximal" and "distal" refer to opposite locations. For example, the proximal end of a syringe is defined as the end closest to the patient, such as a needle port, during insertion or utilization of the syringe. The distal end is the end opposite the proximal end, along the longitudinal direction of the syringe.

Pre-loaded syringes at least partially pre-loaded with an embolic agent are disclosed herein. In some embodiments, the pre-loaded syringe comprises a silicon-free barrel at least partially loaded with the embolic agent and a plunger in communication with an interior surface of the barrel.

In such embodiments, the embolic agent may be dry or may be suspended in a liquid, such as, for example, a carrier liquid comprising saline. In such embodiments, the syringe may comprise a glass barrel or a polymeric barrel.

In some embodiments, the pre-loaded syringe comprises a silicon-free barrel at least partially loaded with a dry embolic agent and a plunger in communication with an interior surface of the barrel. In such embodiments, the syringe may comprise a glass barrel or a polymeric barrel.

In some embodiments, the pre-loaded syringe comprises a silicon-free polymeric barrel at least partially loaded with a dry embolic agent and a plunger in communication with an interior surface of the barrel.

In some embodiments, the pre-loaded syringe comprises a silicon-free polymeric barrel at least partially loaded with a dry embolic agent and a plunger in communication with an interior surface of the barrel, wherein the barrel comprises a lubricant on the interior surface of the barrel.

In any of the foregoing embodiments, the polymeric barrel may comprise any polymeric material, such as, for example, polycarbonate, polypropylene, or cyclo-olefin polymer or copolymer.

In some embodiments, the pre-loaded syringe comprises a silicon-free cyclo-olefin polymer or copolymer barrel at least partially loaded with a dry embolic agent and a plunger in communication with an interior surface of the barrel, wherein the barrel comprises a lubricant on the interior surface of the barrel.

In any of the foregoing embodiments, the embolic agent may comprise a microparticle and/or a microsphere. Examples of microparticles include polyvinyl alcohol (PVA) microparticles, such as Bearing™ non-spherical PVA microparticles. Examples of microspheres include trisacryl cross-linked with gelatin microspheres, such as EmboSphere®, sodium acrylate vinyl alcohol copolymer microspheres, such as HepaSphere®, and polyvinyl alcohol based hydrogels, such as DC Bead®.

In any of the foregoing embodiments, the embolic agent may comprise a polyvinyl alcohol embolic agent. As used herein, "polyvinyl alcohol embolic agent" means any embolic agent that comprises polyvinyl alcohol monomers, such as polyvinyl alcohol polymers and copolymers.

"Dry" as used herein regarding embolic agents and polyvinyl alcohol embolic agents refers to such agents when not suspended in a carrier liquid. The embolic agents, including the polyvinyl alcohol embolic agents, may be coated with various materials, such as aqueous surfactants or lubricants, and still be considered "dry" for the purposes of the present disclosure.

In some embodiments, the pre-loaded syringe comprises a silicon-free cyclo-olefin polymer or copolymer barrel at least partially loaded with a dry polyvinyl alcohol embolic agent and a plunger in communication with an interior surface of the barrel, wherein the barrel comprises a lubricant on the interior surface of the barrel.

In any of the foregoing embodiments, when a lubricant is present on the interior surface of the barrel, the lubricant may comprise a lubricant cross-linked with the interior surface of the barrel. The lubricant may comprise a fluorinated polymer, such as perfluoropolyether (PFPE). Methods of plasma processing PFPE are known in the art and may be used to cross-link PFPE to the interior surface of the barrel with the aid of the present disclosure. See, for example, U.S. Pat. No. 7,431,989 and U.S. Patent Publication No. 2009/

0126404, the contents of each of which are incorporated herein in their entirety by reference.

In any of the foregoing embodiments, the plunger may comprise any polymeric material, such as, for example, acrylonitrile-butadiene-styrene polymer, polycarbonate, polypropylene, or cyclo-olefin polymer or copolymer. The plunger may comprise a tip that is integrally molded with the plunger or attached separately to the plunger. When the plunger is attached separately, the plunger tip may be made of a polymeric material, such as, for example, silicone. Alternatively, the plunger tip may be comprised of a silicon-free material. Additionally, the plunger tip may be lubricated with a silicon-free lubricant.

In any of the foregoing embodiments, the pre-loaded syringe may be configured to be shelf stable for at least six months. Additionally, the pre-loaded syringe may be configured to be shelf stable for at least one year. The pre-loaded syringe may also be configured to be shelf stable for at least two years. Furthermore, the pre-loaded syringe may be configured to be shelf stable for at least three years.

"Shelf stable" as used herein means that any components of the pre-loaded syringe, the embolic agent, and interaction of the embolic agent with the syringe components are such that after the given timeframe (e.g., six months, one year, two years, three years, etc.) the components of the pre-loaded syringe and the embolic agents are still suitable for their intended purpose. For example, when the embolic agent comprises a microparticle or microsphere, significant agglomeration of the embolic agent may render the pre-loaded syringe unsuitable for its intended purpose. In some embodiments, agglomeration of more than about 10% of the embolic agent may render the pre-loaded syringe unsuitable for its intended purpose. Likewise, adhesion of the embolic agent to syringe components, such as the barrel, may also render the pre-loaded syringe unsuitable for its intended purpose. In some embodiments, adhesion of dry embolic agent to components of the syringe may render the pre-loaded syringe unsuitable for its intended purpose. In some embodiments, any visible adhesion of embolic agent to components of the syringe after the embolic agent has been suspended in a liquid may render the pre-loaded syringe unsuitable for its intended purpose.

Additionally, when the embolic agent is to be loaded with a drug, such as, for example, doxorubicin, reduced loading percentage of the embolic agent with the drug may render the pre-loaded syringe unsuitable for its intended purpose. In some embodiments, a reduced loading percentage of more than about 15% as compared to non-aged embolic agent may render the pre-loaded syringe unsuitable for its intended purpose.

In any of the foregoing embodiments, the syringe and components thereof may be sterilization compatible materials. "Sterilization compatible materials," as used herein, refers to materials capable of being sterilized without rendering the materials unsuitable for their intended purpose. If a material is configured for sterilization by at least one method of sterilization without being rendered unsuitable for its intended purpose, then the material is a "sterilization compatible material." For example, a polymeric barrel may deform when autoclaved at temperatures sufficient to sterilize the barrel, rendering the barrel unsuitable for its intended purpose of maintaining a seal with a circular plunger. However, if the same polymeric barrel may be sterilized by another sterilization technique, such as irradiation, and maintain suitability for its intended purpose, then the polymeric material is a "sterilization compatible material."

In any of the foregoing embodiments, the syringe and components thereof may be made from irradiation compatible materials. "Irradiation compatible materials," as used herein, refers specifically to materials capable of being sterilized by irradiation without rendering the materials unsuitable for their intended purpose. For example, a plunger or interior surface of a barrel may comprise a material or lubricant that upon irradiation changes in physical properties such that the syringe is unsuitable for its intended purpose. For example, irradiation may alter certain materials or lubricants such that a syringe using those materials would have an unacceptably high initial peak force required to start movement of the plunger. Or, in another example, irradiation may alter certain materials or lubricants such that a syringe using those materials would have an unacceptably non-uniform force required for travel of the plunger over the length of the barrel or an unacceptably high force required for travel of the plunger over the length of the barrel.

In some embodiments, an unacceptably non-uniform force required for travel of the plunger over the length of the barrel is any non-uniformity that results in user-noticeable "stick-and-slip" of the plunger over the majority of the length of the barrel. The "stick-and-slip" may occur when the static friction forces acting on the plunger (i.e., plunger tip) and the inside of the barrel is not about the same as the kinetic friction forces.

Kits comprising pre-loaded syringes at least partially pre-loaded with an embolic agent are disclosed herein. In some embodiments of the kits, the pre-loaded syringe comprises a silicon-free barrel at least partially loaded with the embolic agent and a plunger in communication with an interior surface of the barrel.

In such embodiments of the kits, the embolic agent may be dry or may be suspended in a liquid, such as, for example, a carrier liquid comprising saline. In such embodiments, the syringe may comprise a glass barrel or a polymeric barrel.

In some embodiments of the kits, the pre-loaded syringe comprises a silicon-free barrel at least partially loaded with a dry embolic agent and a plunger in communication with an interior surface of the barrel. In such embodiments, the syringe may comprise a glass barrel or a polymeric barrel.

In some embodiments of the kits, the pre-loaded syringe comprises a silicon-free polymeric barrel at least partially loaded with a dry embolic agent and a plunger in communication with an interior surface of the barrel.

In some embodiments of the kits, the pre-loaded syringe comprises a silicon-free polymeric barrel at least partially loaded with a dry embolic agent and a plunger in communication with an interior surface of the barrel, wherein the barrel comprises a lubricant on the interior surface of the barrel.

In any of the foregoing embodiments of the kits, the polymeric barrel may comprise any polymeric material, such as, for example, polycarbonate, polypropylene, or cyclo-olefin polymer or copolymer.

In some embodiments of the kits, the pre-loaded syringe comprises a silicon-free cyclo-olefin polymer or copolymer barrel at least partially loaded with a dry embolic agent and a plunger in communication with an interior surface of the barrel, wherein the barrel comprises a lubricant on the interior surface of the barrel.

In any of the foregoing embodiments of the kits, the embolic agent may comprise a microparticle and/or a microsphere. Examples of microparticles include polyvinyl alcohol (PVA) microparticles, such as Bearing™ non-spherical PVA microparticles. Examples of microspheres include trisacryl cross-linked with gelatin microspheres, such as EmboSphere®, sodium acrylate vinyl alcohol copolymer microspheres, such as HepaSphere®, and polyvinyl alcohol based hydrogels, such as DC Bead®.

In any of the foregoing embodiments of the kits, the embolic agent may comprise a polyvinyl alcohol embolic agent.

In some embodiments of the kits, the pre-loaded syringe comprises a silicon-free cyclo-olefin polymer or copolymer barrel at least partially loaded with a dry polyvinyl alcohol embolic agent and a plunger in communication with an interior surface of the barrel, wherein the barrel comprises a lubricant on the interior surface of the barrel.

In any of the foregoing embodiments of the kits, when a lubricant is present on the interior surface of the barrel, the lubricant may comprise a lubricant cross-linked with the interior surface of the barrel. The lubricant may comprise a fluorinated polymer, such as perfluoropolyether (PFPE). Methods of plasma processing PFPE are known in the art and may be used to cross-link PFPE to the interior surface of the barrel with the aid of the present disclosure.

In any of the foregoing embodiments of the kits, the plunger may comprise any polymeric material, such as, for example, acrylonitrile-butadiene-styrene polymer, polycarbonate, polypropylene, or cyclo-olefin polymer or copolymer. The plunger may comprise a tip that is integrally molded with the plunger or attached separately to the plunger. When the plunger is attached separately, the plunger tip may be made of any polymeric material, such as, for example, silicone.

In any of the foregoing embodiments of the kits, the pre-loaded syringe may be configured to be shelf stable for at least six months. Additionally, the pre-loaded syringe may be configured to be shelf stable for at least one year. The pre-loaded syringe may also be configured to be shelf stable for at least two years. Furthermore, the pre-loaded syringe may be configured to be shelf stable for at least three years.

In any of the foregoing embodiments of the kits, the syringe and components thereof may be sterilization compatible materials.

In any of the foregoing embodiments of the kits, the syringe and components thereof may be made from irradiation compatible materials.

Methods of embolizing a blood vessel are also disclosed herein. The methods may comprise removing a syringe pre-loaded with an embolic agent from its packaging. The methods may further comprise filling a barrel of the syringe with a sufficient volume of liquid to suspend the pre-loaded embolic agent. The methods may also comprise injecting the suspended embolic agent into the blood vessel to embolize the blood vessel. The liquid may comprise saline and/or contrast agent. The methods may further comprise agitating the liquid and the pre-loaded embolic agent to mix the two together.

The syringe may comprise any of the pre-loaded syringes and/or kits disclosed above.

EXAMPLES

While various aspects of the embodiments are presented in the examples, the embodiments disclosed herein are not limited by the examples.

Experiments were conducted to determine the shelf stability of different syringes and different syringes pre-loaded with embolic agents.

Example 1

Experiments were conducted to determine the effects of aging on different syringe barrels. All syringes were sterilized by irradiation prior to testing. Syringes to be aged were stored at 56 degrees Centigrade for one month or three months, to simulate storage for one year and three years, respectively. Syringe barrels were tested that comprise a cyclic-olefin polymer (COP) barrel (Zeonex®; Zeon Chemicals, L.P.; Louisville, Ky.). The plungers comprised polycarbonate plastic, with a separate plunger tip made of silicone. These syringes are referred to hereinafter as "COP Syringes." The interior surface of the barrel was lubricated with a fluorinated oil (perfluoropolyether ("PFPE")) cross-linked to the interior surface of the barrel via plasma treatment (TriboGlide™; TriboFilm Research, Inc.; Raleigh, N.C.). COP Syringes so lubricated are referred to hereinafter as "Lubricated COP Syringes."

Figure 2:
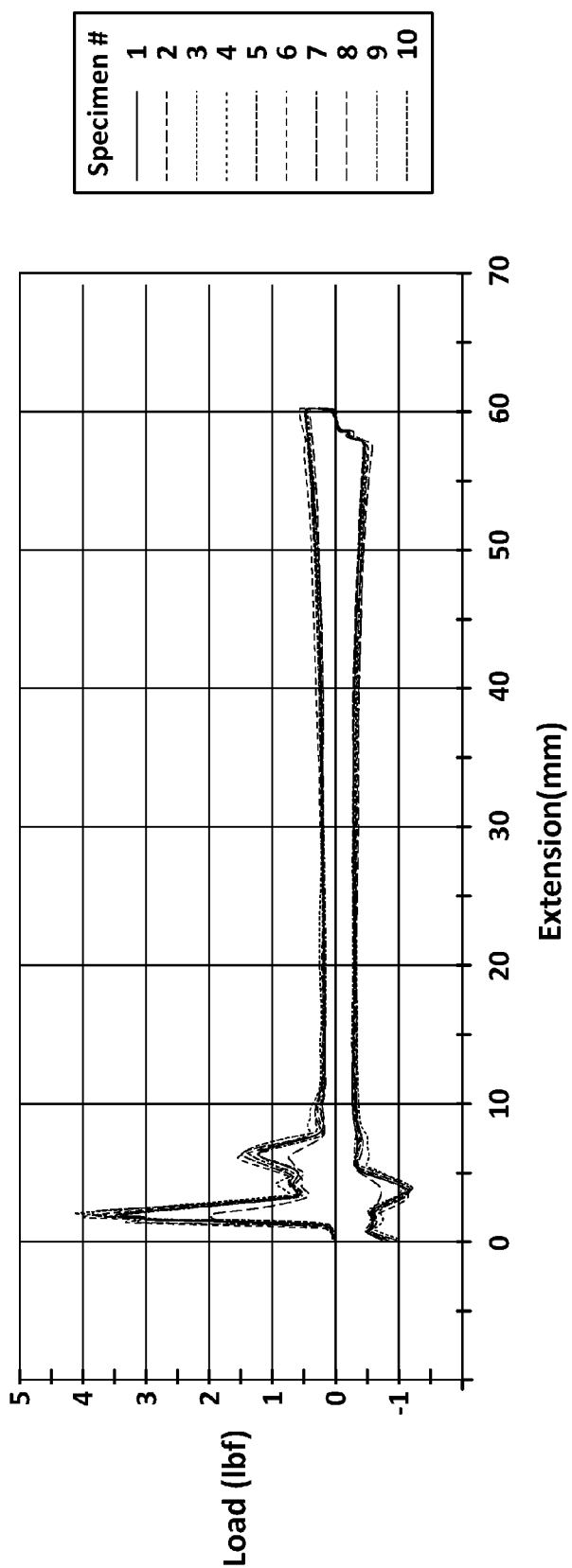
FIG. 2 illustrates the results of force testing with ten syringes that were aged for one month (simulating one year), where the syringes may be used with embodiments of pre-loaded syringes disclosed herein.
Figure 3:
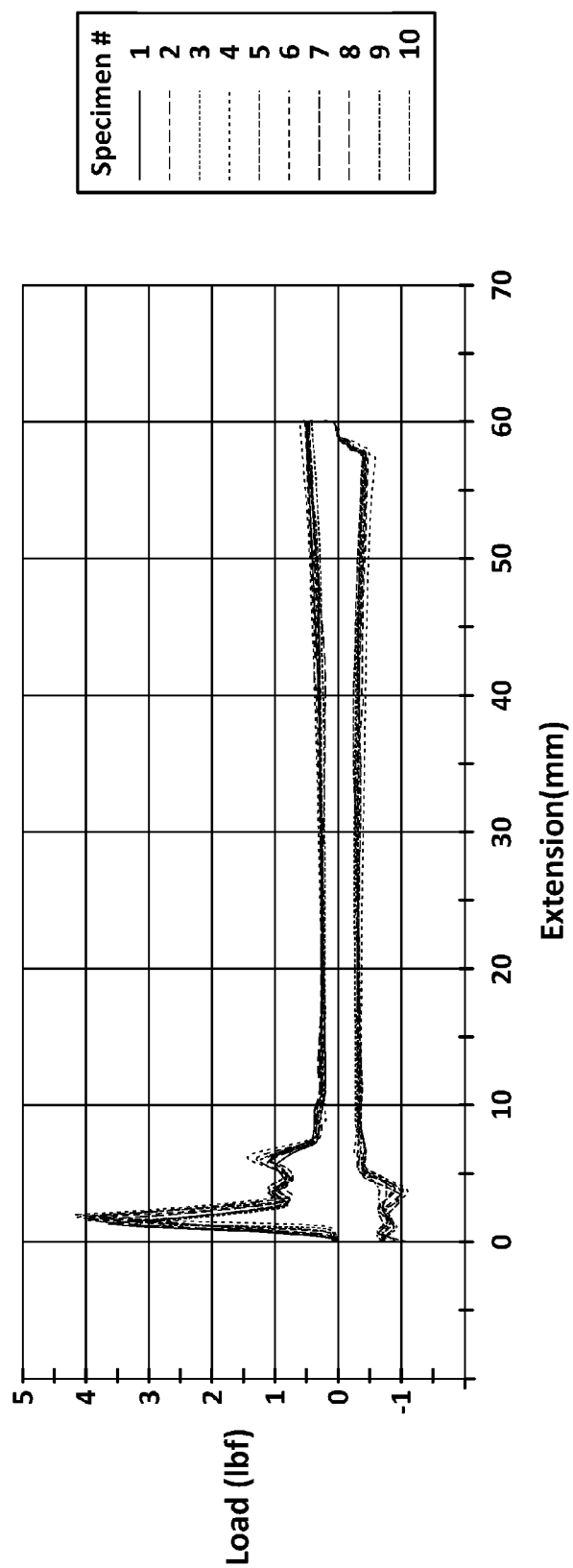
FIG. 3 illustrates the results of force testing with ten syringes that were aged for three months (simulating three years), where the syringes may be used with embodiments of pre-loaded syringes disclosed herein.

FIG. 1 illustrates the results of force testing (load in pounds-force versus plunger extension) with eleven Lubricated COP Syringes that were not aged. FIG. 2 illustrates the results of force testing with ten Lubricated COP Syringes that were aged for one month (simulating one year). FIG. 3 illustrates the results of force testing with ten Lubricated COP Syringes that were aged for three months (simulating three years). The Lubricated COP Syringes had reproducible mechanical behavior regardless of aging.

Example 2

Figure 4:
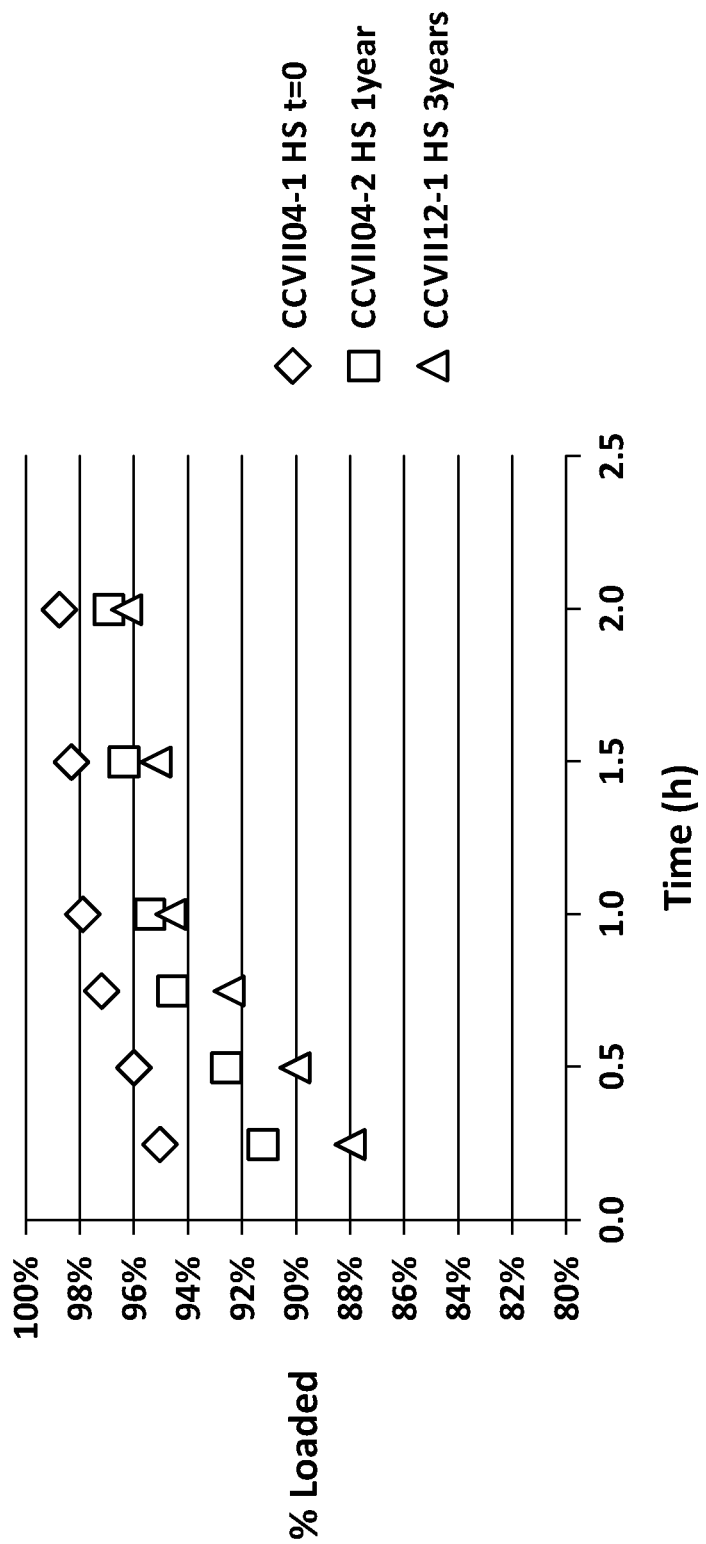
FIG. 4 illustrates doxorubicin loading percentage versus time for embolics loaded in unaged, one-year-aged, and three-year-aged syringes according to one embodiment of a pre-loaded syringe disclosed herein.

Lubricated COP Syringes were filled with sodium acrylate vinyl alcohol copolymer microspheres (HepaSphere®; BioSphere Medical, Inc.; South Jordan, Utah) of the same size. The syringes were sterilized by irradiation. A batch of ten syringes were accelerated-aged one year, and another batch of ten syringes were aged three years, using the aging process of Example 1. FIG. 4 illustrates doxorubicin loading percentage versus time for unaged, one-year-aged, and three-year-aged Lubricated COP Syringes. As can be seen in FIG. 4, doxorubicin loading of the sodium acrylate vinyl alcohol copolymer microspheres in Lubricated COP Syringes was not reduced by more than about 10% at any time. Additionally, within two hours, the loading percentage for the aged sodium acrylate vinyl alcohol copolymer microspheres was about the same as that of the non-aged microspheres.

Example 3

COP Syringes were filled with polyvinyl alcohol (PVA) particles (Bearing™; Merit Medical Inc.; South Jordan, Utah). The syringes were sterilized by irradiation. A batch of ten syringes were accelerated-aged one year, and another batch of ten syringes were aged three years, using the aging process of Example 1. Particle sizes were measured to test for agglomeration of particles over time. The results are shown in Table 1.

TABLE 1

| | Percent of particles in size range | | |
|---|---|---|---|
| Particle size | t = 0 | 1 year | 3 years |
| <100 μm | 0.25 | 0.14 | 1.31 |
| 355-500 μm | 64.37 | 62.57 | 65.24 |
| 255-600 μm | 92.94 | 88.89 | 90.80 |
| >600 μm | 5.28 | 10.13 | 6.79 |

As can be seen in Table 1, there are no significant shifts in particle size as the PVA particles are aged in the COP Syringes. Any agglomeration of particles was less than 10%.

Additionally, no adhesion to the inner surface of the barrel or to the plunger tip was identified.

Hydration time for the PVA particles was somewhat increased for the aged particles in the COP Syringes. Additional samples aged at 40 degrees for the same time periods did not have increased hydration time.

Example 4

Lubricated COP Syringes were filled with polyvinyl alcohol (PVA) particles (Bearing™; Merit Medical Inc.; South Jordan, Utah). The syringes were sterilized by irradiation. A batch of ten syringes were accelerated-aged one year, and another batch of ten syringes were aged three years, using the aging process of Example 1. Particle sizes were measured to test for agglomeration of particles over time. The results are shown in Table 2.

TABLE 2

| Particle size | Percent of particles in size range | | |
|---|---|---|---|
| | t = 0 | 1 year | 3 years |
| <100 μm | 0.25 | 0.14 | 0.16 |
| 355-500 μm | 62.63 | 61.57 | 63.49 |
| 255-600 μm | 91.01 | 87.31 | 90.44 |
| >600 μm | 2.80 | 7.69 | 8.66 |

As can be seen in Table 2, there are no significant shifts in particle size as the PVA particles are aged in the Lubricated COP Syringes. Any agglomeration of particles was less than 10%. Additionally, no adhesion to the inner surface of the barrel or to the plunger tip was identified.

Hydration time for the PVA particles was somewhat increased for the aged particles in the Lubricated COP Syringes. Additional samples aged at 40 degrees for the same time periods did not have increased hydration time. Hydration time for the PVA particles aged in the Lubricated COP Syringes was about the same as for PVA particles aged in COP Syringes.

Example 5

Lubricated COP Syringes were filled with water, sterilized by irradiation, and aged using the process of Example 1. The water was tested for minerals and semi-volatile and non-volatile extractable residues.

Minerals: The water solution was tested by Inductively Coupled Plasma Mass Spectrometry (ICP-MS). Traces of copper, zinc and manganese were found at a concentration lower than 0.1 ppm. Those traces may come from the plunger tip. No significant difference was observed for the three time periods.

Semi-volatile residues: This was tested by Gas Chromatography-Mass Spectrometry (GC-MS). No molecule at a concentration higher than 1 ppm was detected at any aged times.

Non-volatile residues: Tests were performed by Ultra Performance Gas Chromatography Mass Spectrometry (UPLC-MS). No molecules were detected at a concentration higher than 0.1 ppm.

While specific embodiments of pre-loaded syringes and methods of using pre-loaded syringes have been described, it is to be understood that the disclosure provided is not limited to the precise configuration and components disclosed. Various modifications, changes, and variations apparent to those of skill in the art having the benefit of this disclosure may be made in the arrangement, operation, and details of the devices, methods, and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not as a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A pre-loaded syringe comprising:
    a silicon-free polymeric barrel at least partially loaded with a dry embolic agent, wherein the barrel comprises a silicon-free fluorinated lubricant cross-linked with an interior surface of the barrel, wherein the silicon-free fluorinated lubricant comprises a perfluoropolyether; and
    a plunger in communication with the interior surface of the barrel, wherein the plunger comprises a silicon-free plunger tip,
    wherein less than 10% of the dry embolic agent agglomerates after being stored in the barrel for a period of at least six months.

2. The pre-loaded syringe of claim 1, wherein the embolic agent comprises a microsphere.

3. The pre-loaded syringe of claim 1, wherein the dry embolic agent is drug-loadable and exhibits a first loading capacity prior to being loaded in the barrel and a second loading capacity after being stored in the barrel for a period of at least six months, wherein the second loading capacity is within 15% of the first loading capacity.

4. The pre-loaded syringe of claim 1, wherein the syringe comprises sterilization compatible materials.

5. The pre-loaded syringe of claim 1, wherein the syringe comprises irradiation compatible materials.

6. A kit comprising a pre-loaded syringe comprising:
    a silicon-free polymeric barrel comprising a silicon-free perfluoropolyether lubricant cross-linked with en an interior surface of the barrel and at least partially loaded with a dry embolic agent, wherein the dry embolic agent is drug-loadable and exhibits a first loading capacity prior to being loaded in the barrel and a second loading capacity after being stored in the barrel for a period of at least six months, wherein the second loading capacity is within 15% of the first loading capacity; and
    a plunger in communication with the interior surface of the barrel.

7. The kit of claim 6, wherein the embolic agent comprises a polyvinyl alcohol embolic agent.

8. The kit of claim 6, wherein the plunger comprises a silicon-free plunger tip.

9. The kit of claim 8 wherein the polymeric barrel comprises a cyclo-olefin copolymer or a cyclo-olefin polymer.

10. The kit of claim 6, wherein less than 10% of the dry embolic agent agglomerates after being stored in the syringe for a period of at least six months.

11. A method of embolizing a blood vessel, the method comprising:
    removing a syringe pre-loaded with a dry embolic agent from its packaging, wherein the syringe comprises a silicon-free polymeric barrel comprising a silicon-free perfluoropolyether lubricant cross-linked with an interior surface of the barrel, wherein the dry embolic agent comprises a polyvinyl alcohol embolic agent, wherein less than 10% of the dry embolic agent agglomerates after being stored in the syringe for a period of at least six months;

filling the barrel of the syringe with a volume of liquid to suspend the pre-loaded embolic agent; and injecting the suspended embolic agent into the blood vessel to embolize the blood vessel.

12. The method of claim 11, wherein the dry embolic agent is drug-loadable and exhibits a first loading capacity prior to being loaded in the barrel and a second loading capacity after being stored in the barrel for a period of at least six months, wherein the second loading capacity is within 15% of the first loading capacity.

* * * * *